United States Patent
Chae

(10) Patent No.: US 10,549,113 B2
(45) Date of Patent: Feb. 4, 2020

(54) THERAPEUTIC APPARATUS FOR PHOTODYNAMIC THERAPY FOR INVESTIGATING CURVED PORTION

(71) Applicant: THE CATHOLIC UNIVERSITY OF KOREA INDUSTRY-ACADEMIC COOPERATION FOUNDATION, Seoul (KR)

(72) Inventor: Hiun Suk Chae, Seoul (KR)

(73) Assignee: THE CATHOLIC-UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 679 days.

(21) Appl. No.: 14/908,043

(22) PCT Filed: Jul. 28, 2014

(86) PCT No.: PCT/KR2014/006901
§ 371 (c)(1),
(2) Date: Jan. 27, 2016

(87) PCT Pub. No.: WO2015/012670
PCT Pub. Date: Jan. 29, 2015

(65) Prior Publication Data
US 2016/0166846 A1    Jun. 16, 2016

(30) Foreign Application Priority Data

Jul. 26, 2013 (KR) .................. 10-2013-0088868

(51) Int. Cl.
*A61N 5/06* (2006.01)
(52) U.S. Cl.
CPC ............ *A61N 5/062* (2013.01); *A61N 5/0603* (2013.01); *A61N 2005/063* (2013.01); *A61N 2005/0609* (2013.01)

(58) Field of Classification Search
CPC .................. A61N 5/062; A61N 5/0603; A61N 2005/0609; A61N 2005/063
(Continued)

(56) References Cited

U.S. PATENT DOCUMENTS

| 5,381,788 A | 1/1995 | Matula et al. |
| 2010/0168511 A1 | 7/2010 | Muni et al. |

FOREIGN PATENT DOCUMENTS

| JP | 6-154152 A | 6/1994 |
| JP | 3369219 B2 | 1/2003 |

(Continued)

OTHER PUBLICATIONS

International Search Report for PCT/KR2014/006901 dated Nov. 13, 2014.
(Continued)

*Primary Examiner* — Aaron F Roane
(74) *Attorney, Agent, or Firm* — Sughrue Mion, PLLC

(57) ABSTRACT

There is provided a therapeutic apparatus for photodynamic therapy that includes a hollow tube inserted into a living body; an unfolding part that is coupled to one end of the tube and is unfolded; a light irradiation part that is disposed in the unfolding part to irradiate light; and an operating part that is coupled to the other end of the tube to unfold the unfolding part, wherein the light irradiation part irradiates light when the unfolding part is unfolded.
The therapeutic apparatus for photodynamic therapy according to the present disclosure allows irradiation of light by unfolding tissues of the curved portion in the living body, using an unfolding part capable of being unfolded depending on the user's selection and the light irradiation part coupled to the unfolding part, there is an effect of allowing the use of the photodynamic therapy even in a portion that cannot be conventionally treated using the photodynamic therapy.

18 Claims, 9 Drawing Sheets

(58) Field of Classification Search
USPC .......................................................... 607/88
See application file for complete search history.

(56) References Cited

FOREIGN PATENT DOCUMENTS

| JP | 2009-543607 A | 12/2009 |
|----|---------------|---------|
| KR | 10-2011-0111424 A | 10/2011 |
| WO | 2008/008796 A2 | 1/2008 |

OTHER PUBLICATIONS

Written Opinion for PCT/KR2014/006901 dated Nov. 13, 2014.
International Preliminary Report on Patentability for PCT/KR2014/006901 dated Jan. 26, 2016.

THERAPEUTIC APPARATUS FOR PHOTODYNAMIC THERAPY FOR INVESTIGATING CURVED PORTION

CROSS-REFERENCE TO RELATED APPLICATION

This application is a National Stage of International Application No. PCT/KR2014/006901 filed Jul. 28, 2014 claiming priority from Korean Patent Application No. 10-2013-0088868 filed on Jul. 26, 2013, with the Korean Intellectual Property Office, the disclosure of which is incorporated herein by reference.

BACKGROUND

The present disclosure relates to a therapeutic apparatus for removing the causative bacteria of the disease using a photodynamic therapy, and more specifically, to a therapeutic apparatus for photodynamic therapy that is available for a curved portion inside a human body (gastrointestinal tract).

From the past, in the treatment of several pathogens, including bacteria, although the treatment has been performed mainly using antibiotics, according to the use of the antibiotics, recently, a death rate resulting from infection due to pathogen such as several kinds of bacteria (so-called super bacteria) exhibiting resistance to antibiotic has been tended.

Meanwhile, when an antibiotic tolerance of a patient is low or when treatment using the antibiotics is difficult due to allergies to the antibiotics, there is a need for a development of new therapy capable of replacing antibiotics as a therapy against the pathogens.

In order to solve these problems, a photodynamic therapy using light of a particular wavelength has been developed. However, in organs such as a gastrointestinal tract with many curved portions or wrinkles, since irradiation of light is difficult, a sufficient photodynamic therapy is not performed. For example, when considering the anatomy of the stomach, there was a problem in which the irradiation of light was not possible in the extremely curved portion as in FIG. 1 illustrating a cross-sectional view and an endoscopic image of great curvature of stomach, or it was not possible to exhibit an effect even when the irradiation was possible.

Although the therapeutic apparatus for photodynamic therapy according to the present disclosure uses antibiotics as a treatment of the existing microbes using the photodynamic therapy, it is intended to enhance the therapeutic effect by combining the photodynamic therapy with a patient who is not treated due to resistant to antibiotics or the existing antibiotic treatment. However, it is intended to allow the easy treatment of diseases generated from the causative bacteria in order to easily and sufficiently perform the irradiation of light to the curved portion in which the irradiation of light into the human body is difficult. To apply the photodynamic therapy to the curved portion, there is an urgent need for a development of a mechanism that unfolds the curved portion to a flat state to irradiate the light.

The objects of the present disclosure are not limited to those mentioned above, and other problems which are not mentioned will be clearly understood by those skilled in the art from the following description.

SUMMARY

An aspect of the present disclosure may include a tube that is inserted into a living body; a light irradiation part that is installed to be movable in and out of the tube and irradiates light in a state of being discharged to the outside of the tube; and an operating part that moves the light irradiation part to the inside and outside of the tube.

A moving member movable inside the tube may be connected to a rear end of the light irradiation part.

The light irradiation part may include a plurality of optical fiber bundles having leading ends radially unfolded while being discharged to the outside of the tube; and a fixing member in which a leading end is radially unfolded to both sides of the optical fiber bundle.

The fixing member may be elastically supported by an elastic member that provides an elastic force in a direction in which the optical fiber bundle is unfolded.

The moving member may include a rotating part in which the optical fiber bundle is connected to the leading end, the rotating part rotating together with the optical fiber bundle while being discharged to the outside of the tube; and a fixing part in which the rotating part is inserted into the inside and the fixing member is connected to the leading end.

The operating part may rotate the rotating part in a state in which the optical fiber bundle is discharged to the outside of the tube.

The operating part may control the rotational speed of the rotating part in response to an irradiation region in the living body.

The operating part may include a first knob coupled to a rear end of the tube; and a second knob that is rotatably coupled to the first knob and is connected to the moving member.

The sensing part that detects the rotation of the second knob or the contact of the first knob or the second knob may be coupled to the first knob and the second knob to control the operation of the light irradiation part.

Another aspect of the present disclosure may include a hollow tube inserted into a living body; an unfolding part that is coupled to one end of the tube and is unfolded; a light irradiation part that is disposed in the unfolding part to irradiate light; and an operating part that is coupled to the other end of the tube to unfold the unfolding part, the light irradiation part may irradiate light when the unfolding part is unfolded.

The unfolding part includes a plurality of unfolding frames that is inserted into the tube on one side and is coupled to a shaft disposed inside the tube; and variable panels to which the other sides of the plurality of unfolding frames are coupled by being spaced apart from each other, an elongated hole is formed on one side of the unfolding frame coupled to both sides of the variable panel of the plurality of unfolding frames so as to be spaced apart from the shaft, and a sliding rod connected to the operating part is inserted into the elongated hole, thereby making it possible to unfold the variable panel of the unfolding part depending on the position of the sliding rod of the elongated hole.

The elongated hole of the unfolding frame coupled to one side of the variable panel may be formed in a direction facing the elongated hole of the unfolding frame coupled to the other side of the variable panel.

On one side of the tube, a cylindrical cylinder to which the sliding rod is coupled is inserted, and the cylinder may be connected to the operating part.

One end of the variable panel may be formed in an arched shape or a straight line shape.

The operating part may include a first knob coupled to the other end of the tube; and a second knob which is pivotally coupled to the first knob and is connected to the slide rod.

The light irradiation part may be made up of a plurality of light sources coupled to the unfolding frame or the variable panel, a sensor configured to detect the rotation of the second knob or the contact of the first knob and the second knob may be coupled to one side of the first knob or the second knob, thereby controlling the operation of the light source.

The unfolding part is configured to include a plurality of unfolding frames which is inserted into the tube at one side to exert elasticity and is made up of an elastic member connected to the operating part; and variable panels coupled to the other side of each unfolding frame to be spaced apart from each other, the elastic members of each unfolding frame is configured to be mutually unfolded or to approach by operation of the operating part, thereby allowing the unfolding operation and the folding operation of the variable panel.

The elastic members of each unfolding frame may be formed in a twisted form or in a straight line form and may be arranged to intersect with each other.

The therapeutic apparatus for photodynamic therapy according to the present disclosure allows irradiation of light by unfolding tissues of the curved portion in the living body, using an unfolding part capable of being unfolded depending on the user's selection and the light irradiation part coupled to the unfolding part, there is an effect of allowing the use of the photodynamic therapy even in a portion that cannot be conventionally treated using the photodynamic therapy.

Effects of the present disclosure are not limited to those mentioned above, and other effects that haven't not been mentioned will be clearly understood by those skilled in the art from the following description.

BRIEF DESCRIPTION OF DRAWINGS

The above and other aspects, features and other advantages of the present disclosure will be more clearly understood from the following detailed description taken in conjunction with the accompanied drawings, in which.

DETAILED DESCRIPTION

Figure 1:
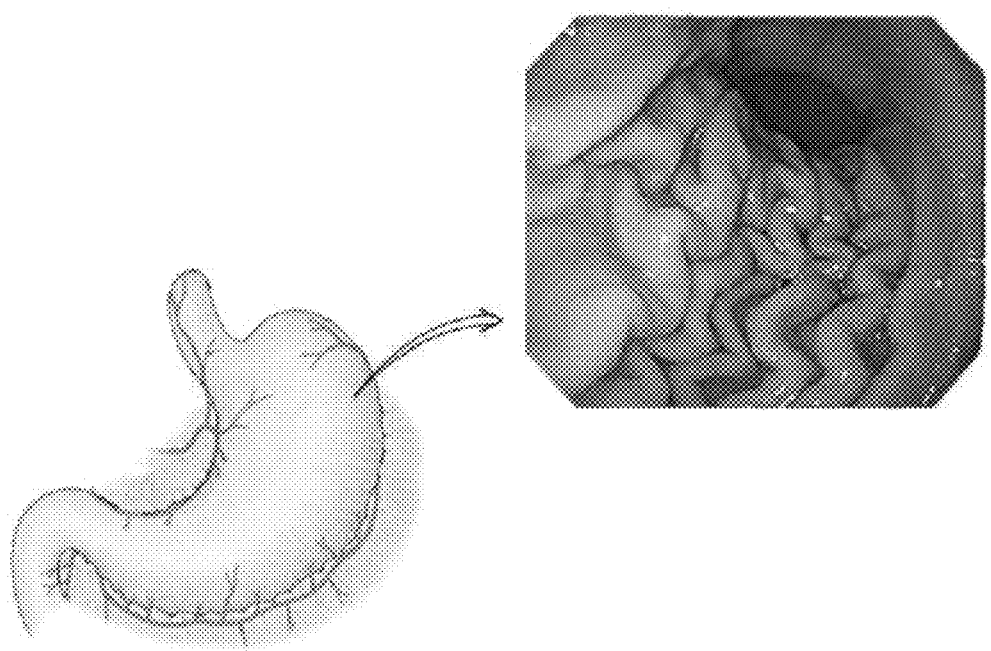
FIG. 1 is a schematic diagram illustrating a stomach of a person and an endoscopic photograph of great curvature of the stomach.

Exemplary embodiments of the present disclosure will now be described in detail with reference to the accompanied drawings.

The disclosure may, however, be exemplified in many different forms and should not be construed as being limited to the specific embodiments set forth herein. Rather, these embodiments are provided so that this disclosure will be thorough and complete, and will fully convey the scope of the disclosure to those skilled in the art.

In the drawings, the shapes and dimensions of elements may be exaggerated for clarity, and the same reference numerals will be used throughout to designate the same or alike elements.

Hereinafter, an exemplary embodiment of a therapeutic apparatus for photodynamic therapy according to the present disclosure will be described in detail with reference to the accompanied drawings.

Figure 2:
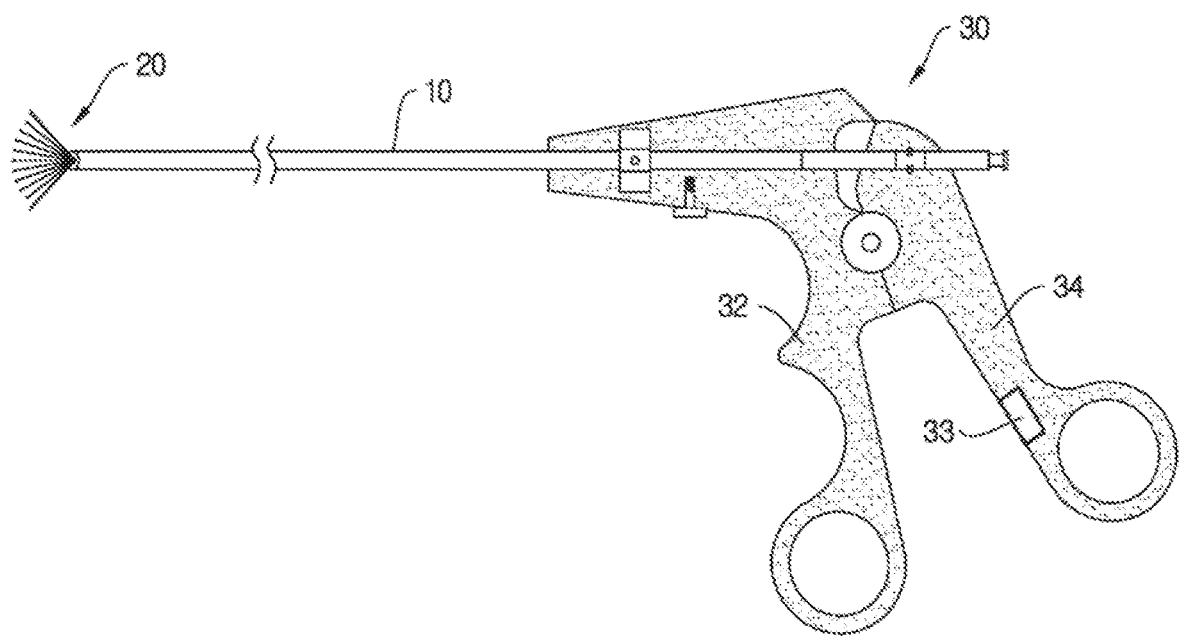
FIG. 2 is a cross-sectional view of a therapeutic apparatus for photodynamic therapy according to an exemplary embodiment of the present disclosure.
Figure 3:
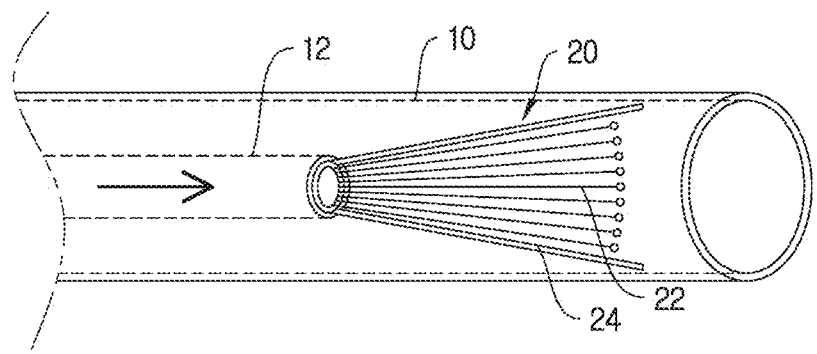
FIG. 3 is an exemplary view illustrating a state in which a light irradiation part is inserted into the tube.
Figure 4:
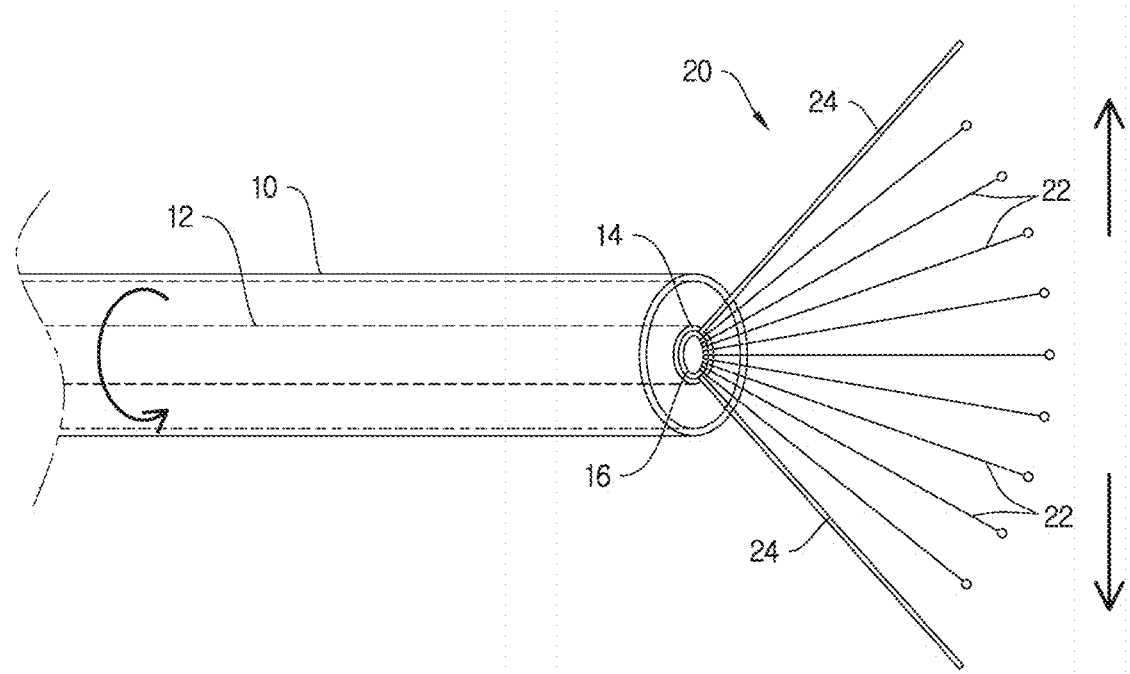
FIG. 4 is an exemplary view illustrating a state in which the light irradiation part is discharged to the outside of the tube.

FIG. 2 is a cross-sectional view of a therapeutic apparatus for photodynamic therapy according to an exemplary embodiment of the present disclosure, FIG. 3 is an exemplary view illustrating a state in which a light irradiation part is inserted into the tube, and FIG. 4 is an exemplary view illustrating a state in which the light irradiation part is discharged to the outside of the tube.

According to the illustrated configuration, the therapeutic apparatus for photodynamic therapy according to the present disclosure may include a tube 10 which is inserted into a living body; a light irradiation part 20 that is installed to be movable in and out of the tube 10 to irradiate light in a state of being discharged to the outside of the tube 10; and an operating part 30 that moves the light irradiation part 20 inside and outside of the tube 10.

The tube 10 is inserted into a living body, and for example, it is desirable to perform the photodynamic therapy, by being inserted into the curved sites or concavo-convex sites (mucosal wrinkle sites) of the inner wall of the living body, such as a gastrointestinal tract.

A moving member 12 is movably mounted inside the tube 10. The moving member 12 is moved inside the tube 10 by the operating part 30, and the moving member 12 is connected to the rear end of the light irradiation part 20. Therefore, when the moving member 12 is moved by the operating part 30, the light irradiation part 20 is moved into and out of the tube 10 in conjunction with this movement. Furthermore, the moving member 12 is usually elastic and can be formed in a rod-like shape that is easily bent.

The moving member 12 can desirably include a tube-shaped fixing part 14, and a rotating part 16 inserted into the fixing part 14. The rotating part 16 is a part in which optical fiber bundles 22 of the light irradiation part 20 are connected, and serves to rotate the optical fiber bundles 22 in a state in which the light irradiation part 20 is moved to the outside of the tube 10. The rotating part 16 is desirably provided only at the leading end of the tube 10 rather than being provided over the entire tube 10, and can rotate by receiving the transmitted power via an electric wire connected to the rear end.

Meanwhile, the light irradiation part 20 can be provided with a light source such as an LED capable of irradiating the light of a particular frequency, depending on the bacteria, and in this embodiment, it is desirably made up of a plurality of optical fibers bundles 22. Of course, in this embodiment, although the light irradiation part 20 has been described as being made up of the optical fiber bundles 22, it is not necessarily limited thereto.

As illustrated in FIG. 4, the leading ends of the optical fiber bundles 22 are desirably radially unfolded, while being discharged to the outside of the tube 10. Thus, when configuring the optical fiber bundles 22 so as to be unfolded on the outside of the tube 10, it is also possible to more effectively irradiate the curved portion in the living body with light.

Further, in this embodiment, when the optical fiber bundles 22 are discharged to the outside of the tube 10 (see FIG. 4), the leading ends are configured to be radially unfolded, and when inserted into the tube 10 (see FIG. 3), it is configured to maintain a pursed shape by the inner wall of the tube 10. Therefore, when the user inserts the tube 10 into a living body, the optical fiber bundles 22 are inserted into the interior of the tube 10 and are easily inserted into the irradiation site, and when reaching the irradiation site the optical fiber bundles 22 are discharged to the outside of the tube 10 to irradiate light.

Meanwhile, the light irradiation part 20 may further include fixing members 24 that are each rotatably mounted to both sides of the optical fiber bundle 22. The fixing members 24 are connected to the leading end of the fixing part 14 of the moving member 12, and serve to evenly unfold the curved portion or uneven portion (mucosal fold) of the inner wall of a living body such as a gastrointestinal tract. That is, the fixing member 24 may be in the shape of a rod. The fixing member may be configured to get unfolded when discharged to the outside of the tube 10 such that the optical fiber bundles 22 can be radially unfolded between both fixing members 24, while maintaining the curved portion or uneven portion in an unfolded state.

The end of the fixing member 24 connected to the moving member 12 can be elastically supported by an elastic member such as a torsion spring so that the fixing member 24 more evenly unfolds the curved portion. In this way, it is possible to more evenly unfold the fixing member 24 into the curved portions of the living body interior wall, by providing an elastic force in a direction in which the optical fiber bundles 22 are unfolded by the elastic member.

Next, the operating part 30 can be operated to rotate the rotating part 16 of the moving member 12 (the fixing part 14 is not operated) in a state in which the light irradiation part 20 is discharged to the outside of the tube 10. Thus, when the optical fiber bundles 22 is rotated together with the rotating part 16, it is possible to more effectively irradiate the curved portion in the living body with light. In other words, when the optical fiber bundles 22 rotate in an unfolded state, since the optical fiber bundles 22 can come into contact with each of the surfaces of the curved portions in the living body, a more effective therapeutic treatment is possible.

At this time, the operating part 30 is capable of controlling the rotational speed of the rotating part 16, depending on the light irradiation area of the living body. For example, in the case of the wide light irradiation area, the operating part 30 increases the rotational speed to more widely unfold the optical fiber bundles 22. In the case of the narrow light irradiation area, the operating part 30 decreases the rotational speed so that the optical fiber bundles 22 can concentrically irradiate light to a narrow area.

Meanwhile, the operating part 30 can include a first knob 32 coupled to the rear end of the tube 10; and a second knob 34 that is rotatably coupled to the first knob 32 and is connected to the moving member 12. A user can rotate the second knob 34, by pursing the fingers after gripping the first knob 32 and the second knob 34 between palm and fingers, and the rotating part 16 can rotate, while the moving member 12 is moved front and back by this action.

Also, the sensing part 33 for sensing the rotation of the second knob 34 or the contact between the first knob 34 and the second knob 32 may be coupled to the first knob 32 or the second knob 34 to control the operation of the light irradiation part 20. For example, the sensing part 33 detects the contact between the first knob 32 and the second knob 34 when a user rotates the second knob 34, and may perform control so that the optical fiber bundle 22 emits light.

Hereinafter, another exemplary embodiment of a therapeutic apparatus for photodynamic therapy according to the present disclosure will be described in detail with reference to the accompanied drawings.

Figure 5:
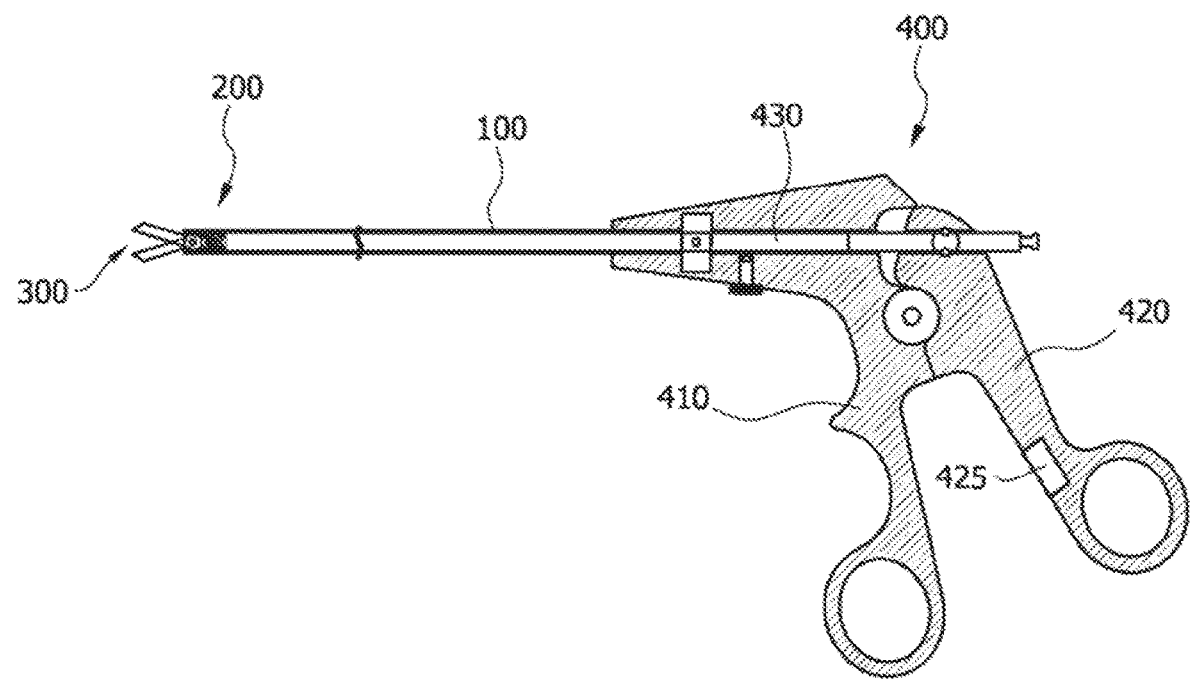
FIG. 5 is a cross-sectional view of a therapeutic apparatus for photodynamic therapy according to another exemplary embodiment of the present disclosure.
Figure 6A:
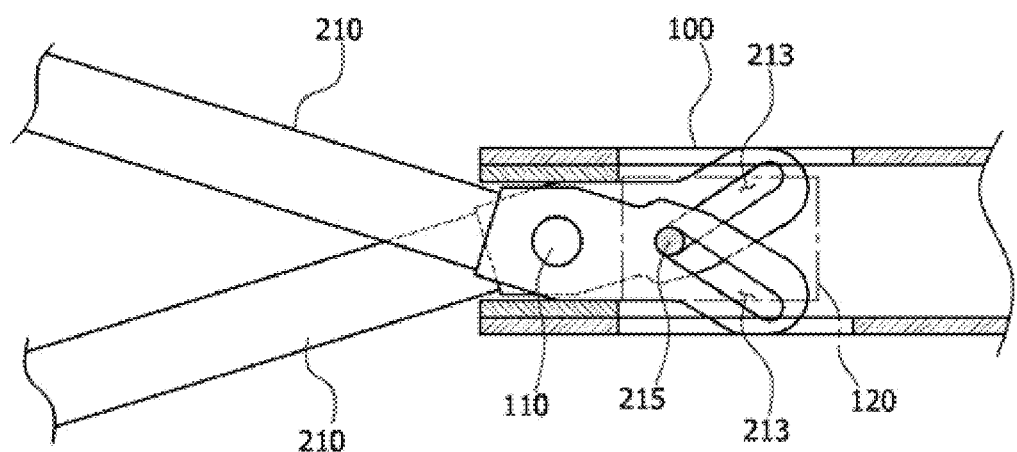
FIGS. 6A and 6B illustrate operation diagrams of an unfolding part illustrated in FIG. 5.
Figure 6B:
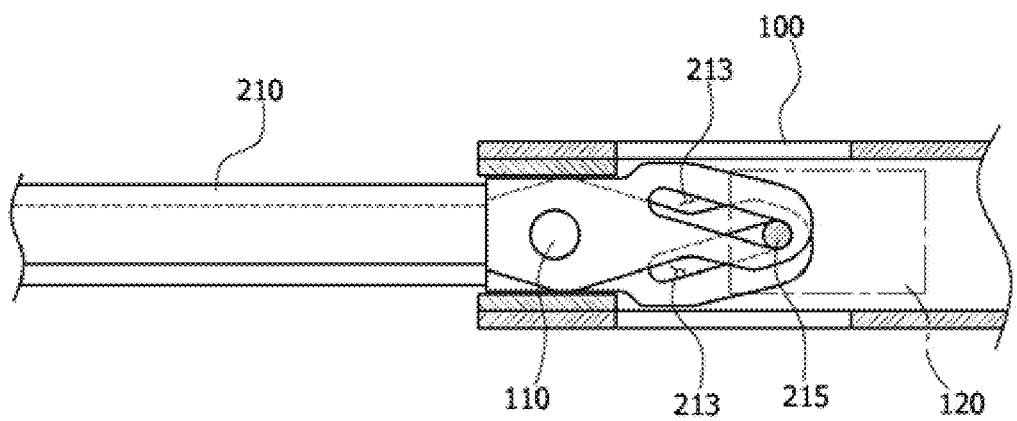

FIG. 5 is a cross-sectional view of a therapeutic apparatus for photodynamic therapy according to another exemplary embodiment of the present disclosure, FIGS. 6A and 6B are operation diagrams of an unfolding part illustrated in FIG. 5, and FIGS. 7A through 7c are plan views illustrating a state in which the unfolding part illustrated in FIG. 5 is unfolded.

Referring to these drawings, the therapeutic apparatus for photodynamic therapy according to another exemplary embodiment of present disclosure includes a hollow tube 100 inserted into a living body, an unfolding part 200 that is coupled to one end of the tube 100 and is unfolded, a light irradiation part 20 that is disposed in the unfolding part 200 to irradiate light, and an operating portion 400 that is coupled to the other end of the tube 100 to unfold the unfolding portion 200.

The tube 100 is inserted into a living body, a through-hole through which one end and the other end communicate with each other is formed inside the tube, and the unfolding part 200 and the operating part 400 are coupled to one end of the tube 100 to operate the unfolding part 200. Thus, after one side of the tube 100 to which the unfolding part 200 is coupled is inserting into a living body, the operating part 400 is operated to unfold the unfolding part 200.

At this time, the light irradiation part 300 is disposed in the unfolding part 200 to be able to irradiate light, when the unfolding part 200 is unfolded.

The unfolding part 200 according to the present disclosure will more specifically be described below with reference to FIGS. 6A and 6B, and FIGS. 7A through 7C.

The unfolding part 200 includes a plurality of unfolding frames 210 coupled to the shaft 110 coupled to the tube 100 so as to be rotated by being inserted into one side of the tube 100, and a variable panel 220 to which distal ends of the plurality of unfolding frames 210 are coupled to be spaced apart from each other.

The unfolding frame 210 is configured to be able to support the entire unfolding part 200, in the unfolding frame 210 formed at both ends of the plurality of unfolding frames 210, an elongated hole 213 in the other direction spaced from the shaft 110 coupled to the tube 100 is formed. The sliding rod 215 connected to an operating part 400 is inserted into the elongated hole 213, and rotates the unfolding frame 210 coupled to both ends of the variable panel 220 of the plurality of unfolding frames 210 around the shaft 110, along the direction of movement of the sliding rod 215. Thus, the variable panel 220 is unfolded when rotating of the unfolding frame 210 coupled to both ends.

As the variable panel 220 gets unfolded while being in contact with the curved portion in a living body, the curved portion may be stretched so that light may be irradiated onto the curved portion effectively.

The elongated holes 213 of the outermost unfolding frames 210 may be formed in different directions as shown in FIGS. 6A-6B and 7A-7C such that the variable panel 220 can be fanned out or folded as the sliding rod 215 moves back and forth in the tube 100.

The sliding rod 215 may be directly connected to the operating portion 400. In this case, however, the connection between the sliding rod 215 and the operating part 400 may be complicated in order to apply the same force to both ends of the sliding rod 215. Thus, it is preferable to connect the sliding rod 215 to the cylindrical cylinder 120 as shown in FIGS. 6A and 6B, and the cylindrical cylinder 120 may be connected to the operating part 400. Further, an elastic body (not illustrated) can be coupled to the cylinder 120 so that the cylinder 120 may return to its original position by elastic force of the elastic body when an external force applied to the cylinder 120 is removed.

Although the operating part 400 can be configured to unfold the unfolding frame 210 by being formed into various shapes, the operating part 400 according to the present disclosure is desirably configured to include a first knob 410 that is coupled to the other end of the tube 100 so that a user can be easily used, and a second knob 420 that is pivotally coupled to the first knob 410 and is connected to the sliding rod 215. Accordingly, it is desirably configured so that a user can rotate the second knob 420, by pursing the fingers after gripping the first knob 410 and the second knob 420 between palm and fingers, and can rotate the sliding rod 215.

In this case, the second knob 420 is connected to the guide bar 430 extending through the tube 100, and the guide bar 430 is connected to the sliding rod 215 or the cylinder 120, during operation of each of the knobs 410 and 420, it pulls the sliding rod 215 or the cylinder 120 or pushes the sliding rod to unfold the unfolding frame 210, or purses the sliding rod to perform the unfolding/folding operations of the variable panel 220.

Figure 7A:
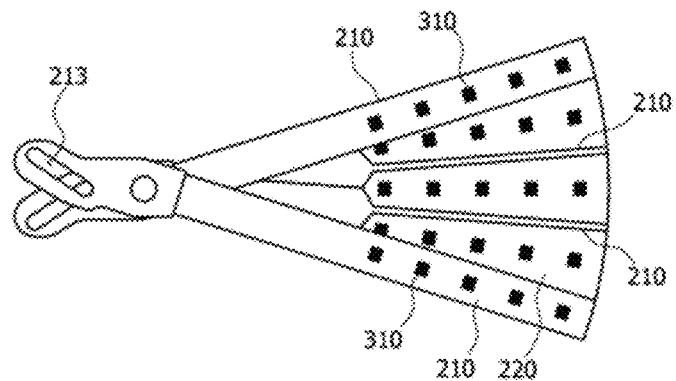
FIGS. 7A through 7C are plan views illustrating a state in which the unfolding part illustrated in FIG. 5 is unfolded.

Referring to FIGS. 7A though 7C, the light irradiation part 300 is made up of a plurality of light sources 310 coupled to the unfolding frame 210 or the variable panel 220, and the sensor 425 (see FIG. 5) for sensing the rotation of the second knob 420 or the contact between the first knob 410 and the second knob 420 is desirably coupled to the one side of the first knob 410 or the second knob 420 to be able to control the operation of the light source 310.

An LED laser fiber or the like can be coupled to the light source 310 to be able to irradiate light of a particular frequency, depending on the causative bacteria, and can also be configured so that a laser is irradiated. The light source 310 is a light source used in a photodynamic therapy and is disclosed in advance in the technical field to which the present disclosure pertains, and thus, the detailed description thereof will be omitted.

Since such a light source 310 is desirably configured to be irradiated only when the variable panel 220 is unfolded, it is desirably configured to detect the rotation of the second knob 420 or to be irradiated only when the first knob 410 and the second knob 420 come into contact with each other.

Therefore, according to the embodiments, the sensor 425 for sensing the rotation angle of the second knob 420 or for sensing the contact or alike can be used.

Figure 7B:
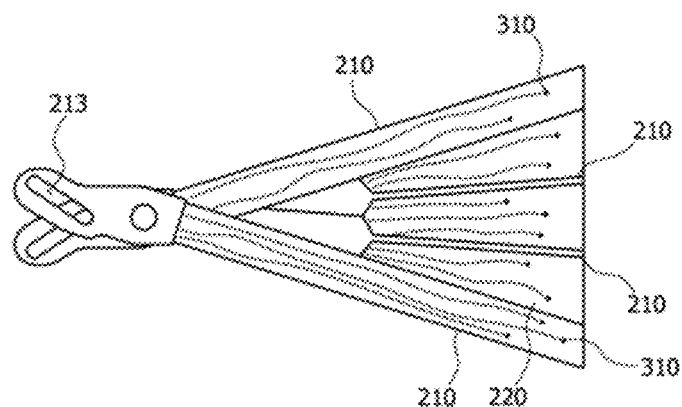
Figure 7C:
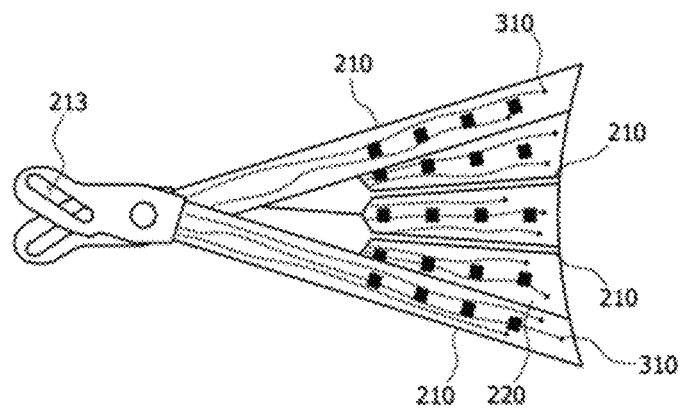

Further, although one end of the variable panel 220 can be formed in various shapes, it can also be convexly formed in other side direction or can also be concavely in one side direction as in FIGS. 7A to 7C so that the curved portions in the body can be effectively unfolded, and may be formed in a straight line shape.

FIGS. 8A and 8B, and FIGS. 9A and 9B illustrate still other examples of the present disclosure, and are configured to operate the variable panel 220 by introducing an elastic member 230 into the unfolding part 200.

First, the unfolding part 200 is made up of a plurality of unfolding frame 210 that exerts resilience by being inserted into the tube 100 on one side and includes an elastic member 230 connected to the operating part 400, and variable panels 220 coupled to the other side of the unfolding frame 210 to be spaced apart from each other.

Here, the elastic members 230 of the unfolding frame 210 are constituted in a twisted form or are configured in a straight line form and are disposed in the form of intersecting with each other.

Furthermore, the one side of each elastic member 230 is exposed to the outside of the tube 100, and an operating part (the guide bar 430 connected to the second knob 420 of the operating part 400) is connected to the other side. Thus, when operating the operating part, each elastic member 230 is pulled and drawn into the tube 100, or is pulled out to unfold or purse the other sides of each unfolding frame 210, thereby allowing the unfolding and the folding operation of the variable panel 220.

In this case, since the leading end of the tube 100 is in contact with the elastic member 230, when the elastic member 230 is drawn into and drawn out of the tube 100, it presses the elastic member 230, thereby allowing such an operation.

Figure 8A:
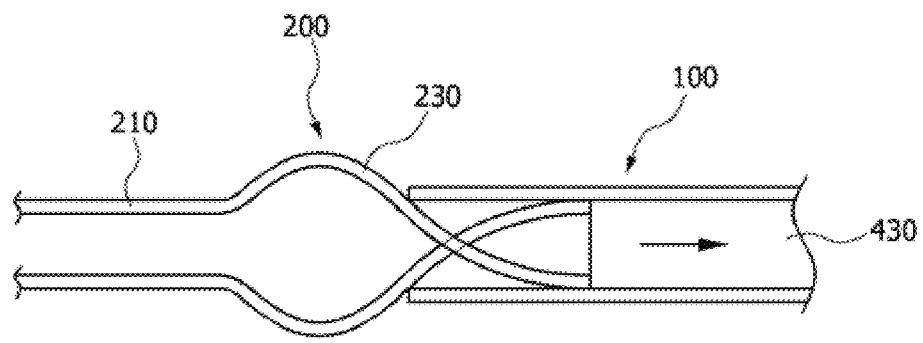
FIGS. 8A and 8B are cross-sectional views of a therapeutic apparatus for photodynamic therapy according to another exemplary embodiment of the present disclosure.
Figure 8B:
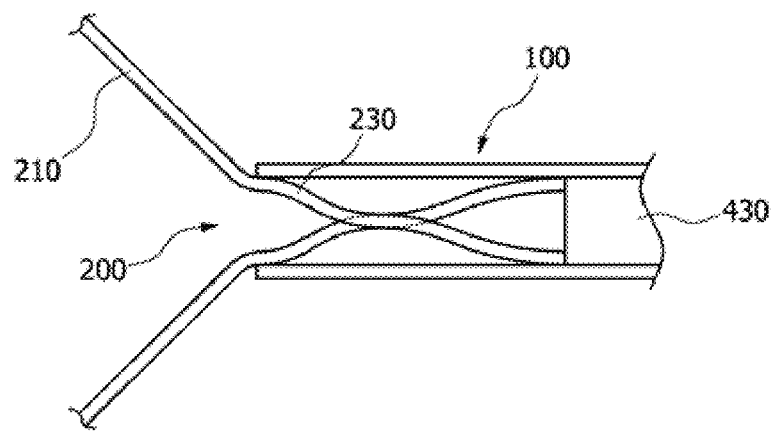

To this end, when the elastic member 230 is configured in a twisted form, each elastic member is initially arranged outside the tube as illustrated in FIG. 8A and in an outward convex state.

At this time, when the guide bar 430 is pulled, the convex portions of each elastic member 230 are pressed by the pulled force and the leading end of the tube 100, and are inverted in a concave form inside the tube, whereby each unfolding frame 210 becomes an unfolded state.

Then, when the guide bar 430 is pressed, the elastic member 230 restores its shape to the convex state, and the unfolding frame 210 reverts to the unfolded state as shown in FIG. 8A.

Figure 9A:
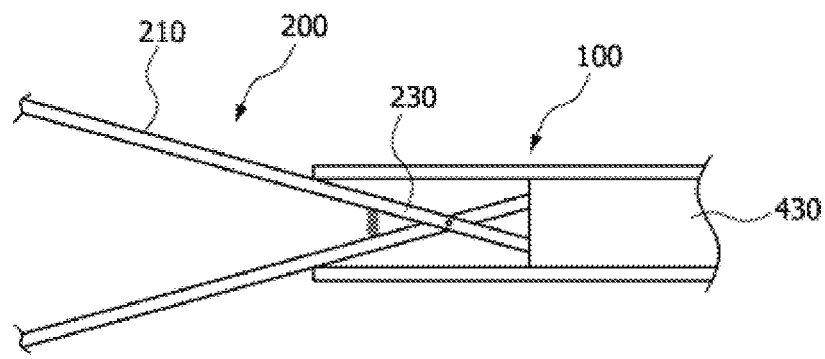
FIGS. 9A and 9B are cross-sectional views of a therapeutic apparatus for photodynamic therapy according to another exemplary embodiment of the present disclosure.
Figure 9B:
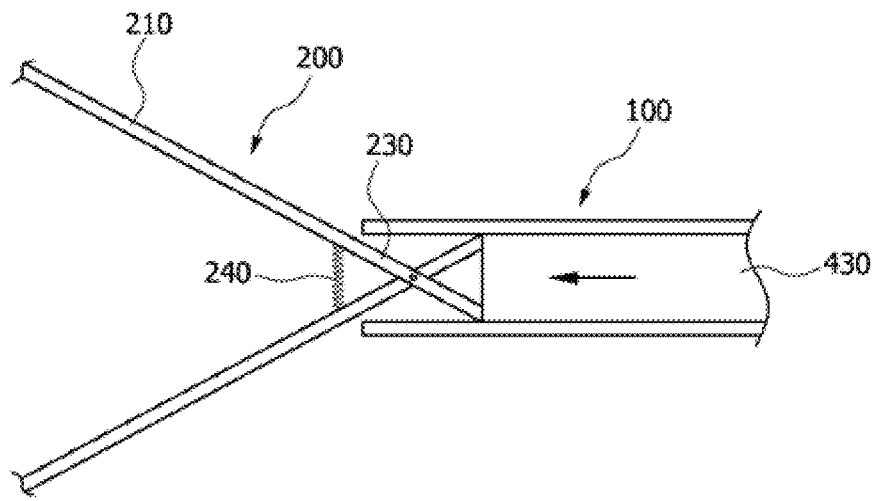

Meanwhile, when the respective elastic members 230 are configured in a straight line form as illustrated in FIGS. 9A and 9B, and are disposed in a cross shape, they are configured to intersect with each other, and the cross points are connected by the shaft.

Further, by introducing the support member 240 such as a spring into each elastic member 230, they are pursed when drawn into the tube 10 and are unfolded when drawn out of the tube 100.

In this case, one end of each elastic member 230 is connected to the guide bar 430 of the operating part 400 and is operated according to the operation of each of the knobs 410 and 420.

At this time, when the elastic member 230 is drawn into the tube 100, the support member 240 is compressed, and when the elastic member 230 is drawn out, the support member 240 is inflated, and one sides of each elastic member 230 are unfolded.

In contrast, when the support member is not introduced, the intersection points of each elastic member 230 are fixed, and when one sides of each elastic member 230 are spaced at a predetermined interval in such a fixed state, when each of the elastic members 230 is drawn into the tube 100, it is pursed, and when drawn out, it exerts the elasticity and is unfolded.

Figure 10A:
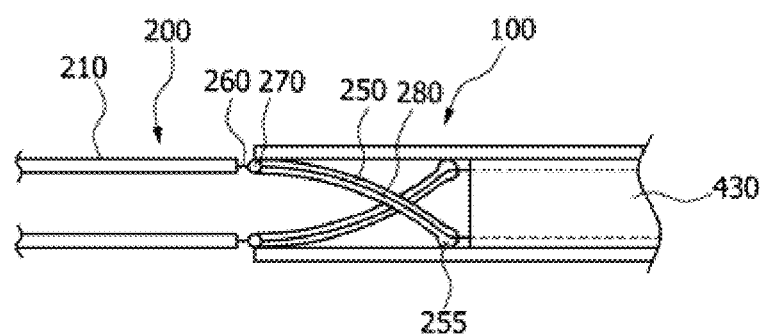
FIGS. 10A and 10B are cross-sectional views of a therapeutic apparatus for photodynamic therapy according to another exemplary embodiment of the present disclosure.
Figure 10B:
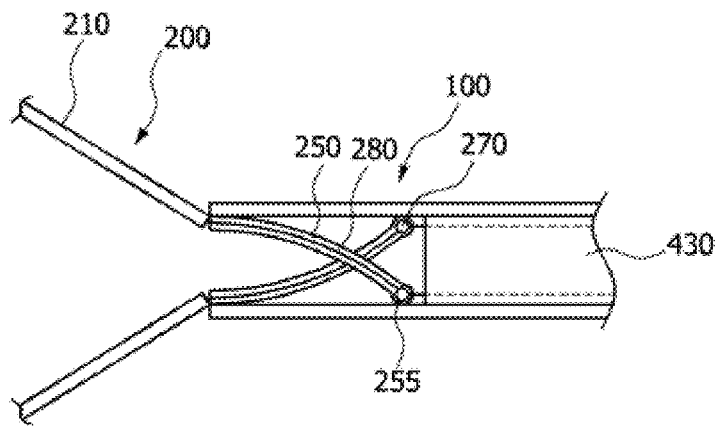

FIGS. 10A and 10B illustrate still another exemplary embodiment of the unfolding part 200 according to the present disclosure, sliding grooves 250 arranged in a manner corresponding to one another and forming a cross-shape when viewed from the side which is formed on the inner surface of the tube 100, and the inner surfaces of the sliding grooves 250 are formed in a helical shape.

Further, a first connecting member 260 having elasticity is provided at one ends of each unfolding frame 210, and balls 270 connected to the end of the first connecting member 260 and inserted into the sliding grooves 250 are provided.

Also, a second connecting member 280 having elasticity is connected to the guide bar 430 of the operating part 400, and each ball 270 is connected to the second connecting member 280.

In the unfolding part 200 configured in this way, when pressing the respective knobs 410 and 420 of the operating part 400 to come close to each other, the guide bar 430 is pulled, and simultaneously, each ball 270 moves in the inward direction of the tube 100 while riding on the sliding grooves 250 by the second connecting member 280, and the second connecting member 280 is in an inflated state.

At this time, each ball 270 moves to intersect with each other along the sliding grooves 250, and each unfolding frame 210 is gradually opened by the first connecting member 260, and the first connecting member 260 is also in an inflated state.

When each ball 270 is moved and located at the end of the sliding groove 250, the interval of each unfolding frame 210 is maximally open, and the variable panel 220 is completely unfolded.

Furthermore, one end of each unfolding frame 210 preferably rest on the leading end of the sliding groove 250 to be prevented from entering the sliding groove 250, so that the unfolding operation of each unfolding frame 210 can be smoothly performed.

When the respective knobs 410 and 420 of the operating part 400 are manipulated to move away from each other, the guide bar 430 moves forward, and simultaneously, the second connecting member 280 and the first connecting member 260 shrink. Also, each ball 270 moves in the outward direction of the tube 100, while riding on the sliding groove 250.

Thus, as each ball 270 moves in an outward direction of the tube 100 while riding on the sliding groove 250, while each unfolding frame 210 is gradually folded, when each ball 270 is located at the leading end of the sliding groove 250, the tube is completely folded, and simultaneously, the variable panel 220 is also folded.

Furthermore, the leading end or the distal end or both ends of the sliding groove 250 are formed with receiving grooves 255 so that the balls 270 can sit thereon, and when the balls 270 are located at the leading end and the distal end, the grooves can also preferably perform a stopper so that the balls can be stopped at that position.

The exemplary embodiments described in the specification and the accompanied drawings merely exemplarily explain some of the technical ideas contained in the present disclosure. Thus, since the exemplary embodiments disclosed herein are intended to illustrate the technical spirit of the present disclosure rather than limit the same, it is obvious that the scope of the technical idea of the present disclosure is not limited by the exemplary embodiments. Modifications and specific examples that can be easily analogized within the scope of the technical idea included in the specification and the drawings of the present disclosure by those skilled in the art should be construed as being included in the scope of right of the present disclosure.

While exemplary embodiments have been illustrated and described above, it will be apparent to those skilled in the art that modifications and variations could be made without departing from the spirit and scope of the present disclosure as defined by the appended claims.

What is claimed is:

1. A therapeutic apparatus for photodynamic therapy comprising:
   a tube;
   a light irradiation part configured to slide into and out of the tube and irradiate light in response to being discharged to an outside of the tube; and
   an operating part configured to move the light irradiation part into and out of the tube.

2. The therapeutic apparatus for photodynamic therapy of claim 1, further comprising a moving member configured to move inside the tube and connected to a rear end of the light irradiation part.

3. The therapeutic apparatus for photodynamic therapy of claim 2, wherein the light irradiation part comprises:
   an optical fiber bundle having leading ends which are radially unfolded in response to being discharged to the outside of the tube; and
   fixing members having leading ends which are radially unfolded at both sides of the optical fiber bundle.

4. The therapeutic apparatus for photodynamic therapy of claim 3, wherein the fixing members are elastically supported by an elastic member that provides an elastic force in a direction in which the optical fiber bundle is unfolded.

5. The therapeutic apparatus for photodynamic therapy of claim 3, wherein the moving member comprises:
   a rotating part to which the optical fiber bundle is connected such that the rotating part rotates together with the optical fiber bundle when the optical fiber bundle is discharged to the outside of the tube; and
   a fixing part in which the rotating part is inserted, wherein the fixing members are connected to a leading end of the fixing part.

6. The therapeutic apparatus for photodynamic therapy of claim 5, wherein the operating part is configured to rotate the rotating part when the optical fiber bundle is discharged to the outside of the tube.

7. The therapeutic apparatus for photodynamic therapy of claim 5, wherein the operating part is configured to control a rotational speed of the rotating part based on an irradiation region in a living body.

8. The therapeutic apparatus for photodynamic therapy of claim 2, wherein the operating part comprises a first knob coupled to a rear end of the tube; and
   a second knob that is rotatably coupled to the first knob and is connected to the moving member.

9. The therapeutic apparatus for photodynamic therapy of claim 8, further comprising a sensing part configured to detect rotation of the second knob or contact between the first knob and the second knob, and control an operation of the light irradiation part based on the rotation or the contact.

10. A therapeutic apparatus for photodynamic therapy comprising:
    a hollow tube;
    an unfolding part that is coupled to one end of the tube and is foldable;
    a light irradiation part that is disposed in the unfolding part to irradiate light; and
    an operating part that is coupled to the other end of the tube to unfold the unfolding part, wherein the light irradiation part irradiates configured to irradiate light in response to being unfolded.

11. The therapeutic apparatus for photodynamic therapy of claim 10, wherein the unfolding part comprises:
a plurality of unfolding frames of which one ends are inserted into the tube and coupled to a shaft disposed inside the tube; and
variable panels to which the other ends of the plurality of unfolding frames are coupled such that the variable panels are spaced apart,
wherein elongated holes are formed on one side of the unfolding frames coupled to both sides of the variable panels so as to be spaced apart from the shaft, and a sliding rod connected to the operating part is inserted into the elongated holes, thereby unfolding the variable panels of the unfolding part depending on a position of the sliding rod of within the elongated holes.

12. The therapeutic apparatus for photodynamic therapy of claim 11, wherein an elongated hole of an unfolding frame coupled to one side of the variable panels is formed in a direction facing an elongated hole of an unfolding frame coupled to the other side of the variable panels.

13. The therapeutic apparatus for photodynamic therapy of claim 11, wherein on one side of the tube, a cylindrical cylinder to which the sliding rod is coupled is inserted, and the cylinder is connected to the operating part.

14. The therapeutic apparatus for photodynamic therapy of claim 11, wherein one end of the variable panels is formed in an arched shape or a straight line shape.

15. The therapeutic apparatus for photodynamic therapy of claim 11, wherein the operating part comprises:
a first knob coupled to the other end of the tube; and
a second knob which is pivotally coupled to the first knob and is connected to the slide rod.

16. The therapeutic apparatus for photodynamic therapy of claim 15, wherein the light irradiation part is made up of a plurality of light sources coupled to the unfolding frames or the variable panels,
a sensor configured to detect the rotation of the second knob or contact between the first knob and the second knob, and control an operation of the light sources based on the rotation or the contact.

17. The therapeutic apparatus for photodynamic therapy of claim 10, wherein the unfolding part comprises:
a plurality of unfolding frames which are inserted into the tube at one ends to exert elasticity and comprises elastic members connected to the operating part; and
variable panels coupled to the other ends of the unfolding frames such that the variable panels are spaced apart,
wherein the elastic members of each the unfolding frames are configured to be mutually unfolded or to approach by operation of the operating part, thereby allowing an unfolding operation and a folding operation of the variable panels.

18. The therapeutic apparatus for photodynamic therapy of claim 17, wherein the elastic members are formed in a twisted form or a straight line form and arranged to intersect with each other.

* * * * *